United States Patent [19]

Pelosi, Jr.

[11] 4,002,621
[45] Jan. 11, 1977

[54] 6-CHLORO-2-(3,4-DICHLOROANILINO)-4H-3,1-BENZOTHIAZINE

[75] Inventor: Stanford Salvatore Pelosi, Jr., Norwich, N.Y.

[73] Assignee: Morton-Norwich Products, Inc., Norwich, N.Y.

[22] Filed: Oct. 30, 1975

[21] Appl. No.: 627,227

[52] U.S. Cl. .......................... 260/243 R; 424/246
[51] Int. Cl.² ................................. C07D 279/08
[58] Field of Search ............................... 260/243 R

[56] References Cited
UNITED STATES PATENTS 3,417,085   12/1968   Kuch et al. .................. 260/243

Primary Examiner—John M. Ford
Attorney, Agent, or Firm—Anthony J. Franze

[57] ABSTRACT

6-Chloro-2-(3,4-dichloroanilino)-4H-3,1-benzothiazine is an effective antibacterial agent.

1 Claim, No Drawings

6-CHLORO-2-(3,4-DICHLOROANILINO)-4H-3,1-BENZOTHIAZINE

This invention relates to the compound 6-chloro-2-(3,4-dichloroanilino)-4H-3,1-benzothiazine of the formula:

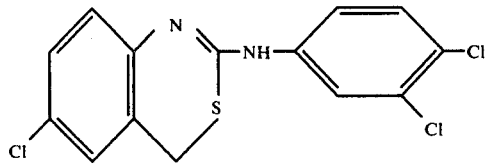

and a method for its preparation.

The compound of this invention possesses antibacterial activity. It is particularly inimical to *Staphylococcus aureus, Streptococcus faecialis, Corynebacterium liquefaciens, Hemophilus vaginalis,* and *Streptococcus agalactiae* in the commonly employed in vitro technique for determining antibacterial activity at levels of from 0.75 to 12.5 mcg of compound per milliliter of test media. It is thus adapted to be combined in various forms such as ointments, powders, solutions, sprays, dusts, and the like in a concentration of from 0.1–1% by weight suitable for application to prevent bacterial contamination.

The compound of this invention is readily prepared. Currently it is preferred to react 3,4-dichloroaniline with 6-chloro-2-methylthio-4H-3, 1-benzothiazine. In order that this invention may be fully available to and understood by those skilled in the art, the method now preferred is briefly described.

6-Chloro-4H-3,1-benzothiazine-2(1H)thione

Carbon disulfide (180 ml, 3.0 moles) was added dropwise to a stirred solution of 84 g (1.5 moles) of potassium hydroxide in 400 ml of absolute ethanol with external cooling. To this mixture was added 157 g (1.0 mole) of 2-amino-5-chlorobenzyl alcohol. The reaction mixture was heated under relux for 20 hours and the solvent was removed by distillation. The solid residue was stirred with 2000 ml of 10% aqueous potassium hydroxide, and the mixture was filtered to remove neutral impurities. The clear filtrate was made acidic with dil. hydrochloric acid, and the solid which was deposited was collected by filtration to give 221 g (100%) of product. Recrystallization from methanol gave an analytical sample, m.p. 217°–222°.

Anal. Calcd. for $C_8H_6NS_2$ CL: C, 44.54; H, 2.80; N, 6.49;
S, 29.73; Cl, 16.44.
Found: C, 44.79; H, 2.87; N, 6.46;
S, 29.84, 29.67; Cl, 16.63, 16.45.

6-Chloro-2-methylthio-4H-3,1-benzothiazine Hydrochloride

Dimethyl sulfate (34 ml, 0.36 mole) was added dropwise to a stirred mixture of 77 g (0.36 mole) of the above compound in 150 ml (0.36 mole) of 10% sodium hydroxide solution with external cooling to maintain the temperature below 40°. The mixture was stirred at ambient temperature for 4 hours, and the solid was collected by filtration to give 80 g (96%) of yellow solid. Recrystallization from a methanol-water mixture gave 43 g (52%) of free base of product. A suspension of 3.0 g (0.013 mole) of this material in 25 ml of acetonitrile was treated with hydrogen chloride and heated to boiling. Additional acetonitrile and absolute ethanol were were added for dissolution. With cooling in ice and the addition of anhydrous ether, a solid separated which was collected by filtration to give 2.3 g (66%) of product, m.p. 134°–137°.

Anal. Calcd. for $C_9H_8ClNS_2.HCl$: C, 40.60; H, 3.41; N, 5.26;
S, 24.09; Cl, 26.64.
Found: C, 40.78; H, 3.48; N, 5.33;
S, 24.06, 24.10; Cl, 26.63, 26.69.

6-Chloro-2-(3,4-dichloroanilino)-4H-3,1-benzothiazine

A mixture of 92 g (0.40 mole) of the free base of the above compound and 65 g (0.40 mole) of 3,4-dichloroaniline in 300 ml of n-butanol was heated under reflux for 17 hours. After concentration of the solvent and cooling in a refrigerator for several days, the solid was collected by filtration. Recrystallization from ethanol-water mixture gave 69 g (51%) of product, m.p. 170°–172°.

Anal. Calcd. for $C_{14}H_9CL_3N_2S$: C, 48.93; H, 2.64; N, 8.15;
S, 9.33; Cl, 30.95.
Found: C, 49.03; H, 2.62; N, 8.22;
S, 9.29. 9.33; Cl, 30.76, 30.95.

What is claimed is:

1. The compound 6-chloro-2-(3,4-dichloroanilino)-4H-3, 1-benzothiazine of the formula:

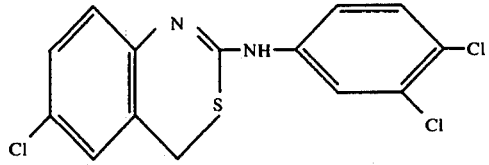

* * * * *